United States Patent [19]

Wilson et al.

[11] Patent Number: 4,696,676
[45] Date of Patent: Sep. 29, 1987

[54] USE OF 1-NONEN-3-OL FOR REPELLING INSECTS

[75] Inventors: Richard A. Wilson, Westfield, N.J.; Jerry F. Butler, Gainesville, Fla.; Donald Withycombe, Lincroft; Braja D. Mookherjee, Holmdel, both of N.J.; Ira Katz, West Long Branch; Kenneth R. Schrankel, Tinton Falls, both of N.J.

[73] Assignees: International Flavors & Fragrances Inc., New York, N.Y.; The University of Florida, Gainesville, Fla.

[21] Appl. No.: 2,020

[22] Filed: Jan. 9, 1987

Related U.S. Application Data

[62] Division of Ser. No. 879,426, Jun. 27, 1986.

[51] Int. Cl.⁴ .............................................. C10L 5/00
[52] U.S. Cl. ........................................ 44/7.5; 424/83; 424/78; 512/4
[58] Field of Search ................... 424/78, 83, DIG. 10; 514/739, 919; 44/7.5; 252/522 R, 522 A

[56] References Cited

U.S. PATENT DOCUMENTS

| | | | |
|---|---|---|---|
| 2,043,941 | 6/1936 | Williams | 167/22 |
| 2,254,665 | 9/1941 | Ralston et al. | 167/22 |
| 3,615,289 | 10/1971 | Felton | 44/7.5 |
| 3,645,705 | 2/1972 | Miller | 44/7.5 |
| 4,051,159 | 9/1977 | Tsoucalas et al. | 260/404.5 |
| 4,152,422 | 5/1979 | Ohinata et al. | 424/84 |
| 4,168,248 | 9/1979 | Kulka | 252/522 R |
| 4,364,931 | 12/1982 | Szantay et al. | 424/84 |
| 4,449,987 | 5/1984 | Lindauer | 44/7.5 |
| 4,618,627 | 10/1986 | Murase et al. | 514/678 |

OTHER PUBLICATIONS

Chem. Abstracts, vol. 103, 1974, No. 71086p, "The Synthesis of (Z)-8-dodecen-1-ol and its Acetate, Pheromone Components of the Oriental Fruit Moth (*Grapholita molesta*)", Akrust, et al., Acta. Chem. Scand., Ser. B, (1985), B39(4), 267-72.

Chem Abstracts, vol. 80, 1974, No. 117098f, "Trans-6-nonen-1-ol acetate, Ovipositional Attractant and Stimulant of the Melon fly", Keiser et al., *J. Econ. Entomol*, 1973, 66(6), 1355-6.

Burton, "Intrinsic Mosquito Repellency Values of some Chemical Compounds", American Perfumer and Cosmetics, Apr. 1969, p. 41.

Chem. Abstracts, vol. 74, 1971, No. 99419f, "Synthetic Nonenyl Acetate as Attractants for Female Melon Flies", Martin, et al., *J. Med. Chem., 1971, 14(3), 236-239*.

Primary Examiner—Peter A. Nelson
Attorney, Agent, or Firm—Arthur L. Liberman

[57] ABSTRACT

Described is the use of 1-nonen-3-ol as a repellent for house flies (*Musca domestica*). Also described are candle compositions which may be opaque or transparent or pastel shaded which are adapted to incorporate 1-nonen-3-ol which are both perfumes and insect repellents without flashing during burning. Such compositions comprising as the basic components a mixture of (a) a hydrocarbon wax or (b) a thermoplastic polyamide resin formed from linoleic acid polymerized with a polyamide compound taken together with an alkanol amide or alkanol amine and a stearic acid compound or (c) a straight chain aliphatic amide in combination with light mineral oil and alcohol; compositions (a), (b) or (c), supra, taken further together with 1-nonen-3-ol taken alone or together with a perfume composition substantially inactive from an insect repellent standpoint.

3 Claims, 3 Drawing Figures

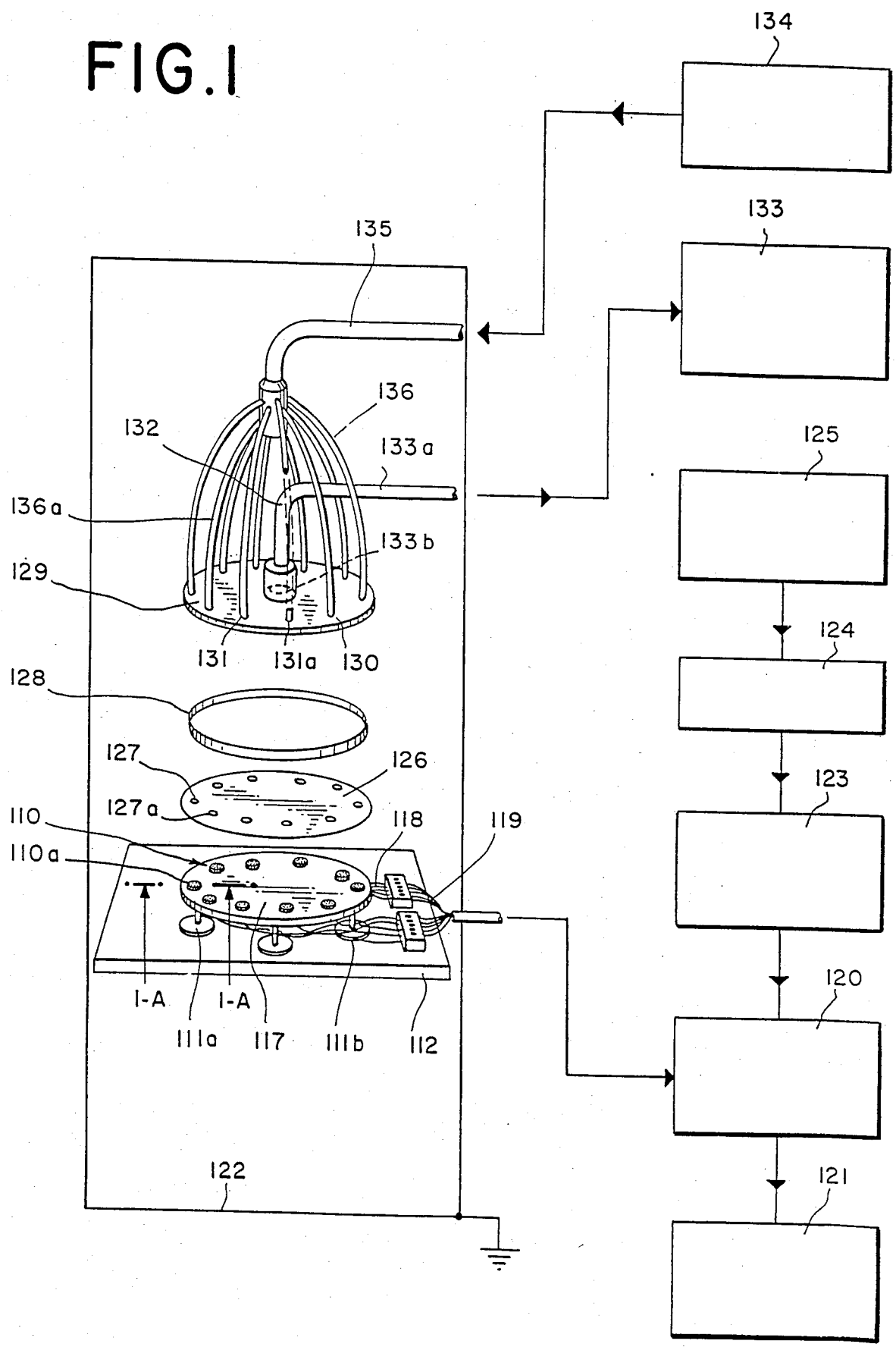

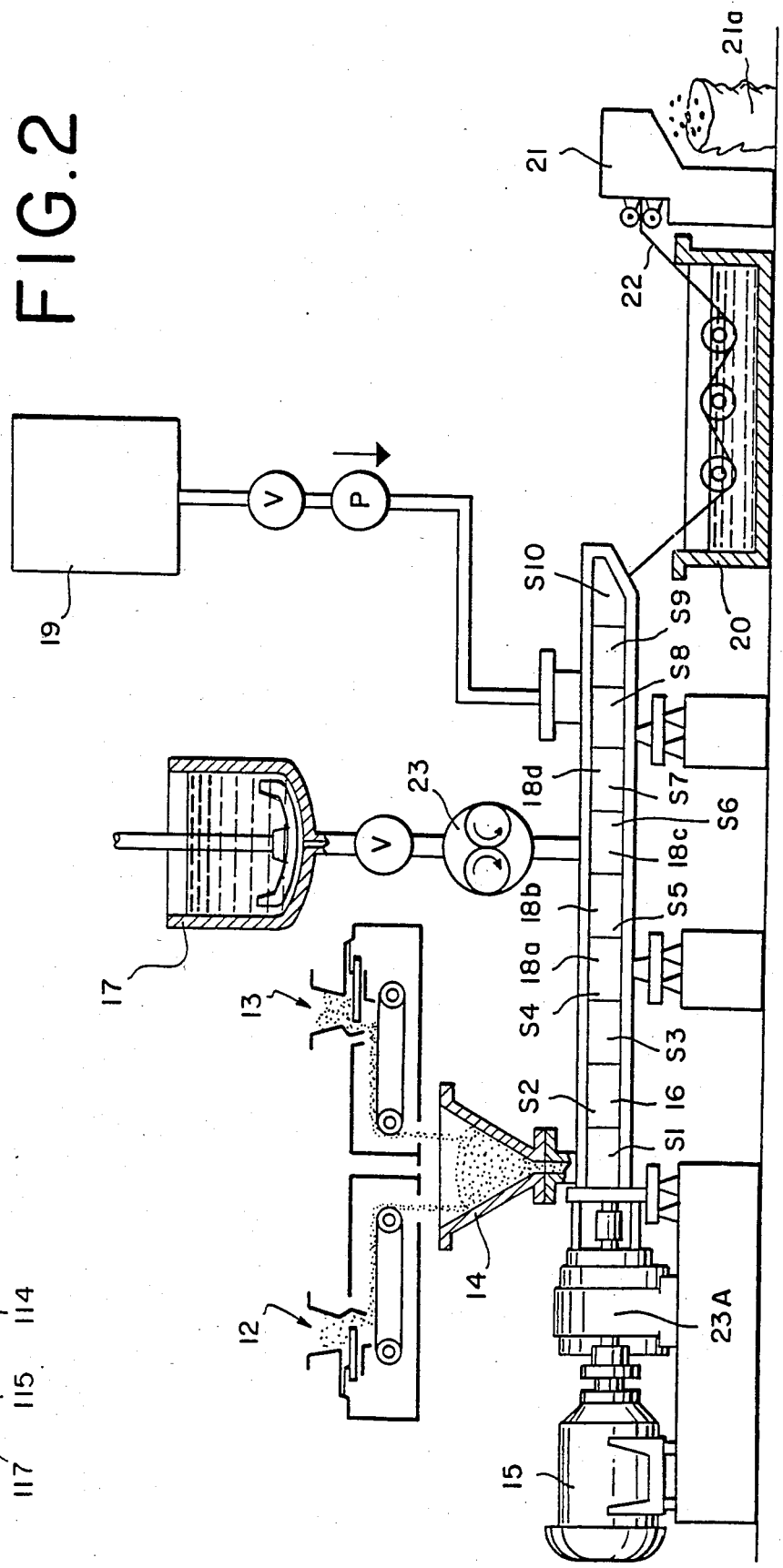

USE OF 1-NONEN-3-OL FOR REPELLING INSECTS

This is a divisional of application Ser. No. 879,426, filed June 27, 1986, pending.

BACKGROUND OF THE INVENTION

This invention relates to the use of 1-nonen-3-ol as a repellent for house flies (*Musca domestica*) and further it relates to materials suitable for candle bodies which candle bodies include compositions of matter which are both (i) efficaciously insect repelling and (ii) perfuming in an aesthetically pleasing manner on use thereof.

Formulations exist in commerce which are said to provide adequate insect repellent properties, e.g., those set forth in U.S. Pat. No. 2,043,941 which indicate the repellency properties of methallyl disulfide having the structure:

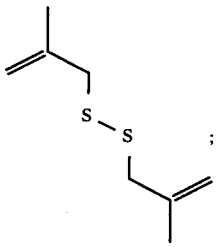

and those set forth in U.S. Pat. No. 4,449,987 issued on May 22, 1984 which indicate the combination of methyl heptenones, coumarin and indole for use in perfumed candles.

However, efficacious compositions of matter taken alone or for use in combination with perfumes for repelling house flies have not yet been developed.

Unsaturated alcohols and esters thereof are known with respect to controlling insects; however, they have been found to attract rather than repel such insects. Thus, U.S. Pat. No. 4,152,422 issued on May 1, 1979 sets forth 6-nonen-1-ol in a composition of matter used as an attractant for the male Mediterranean Fruit Fly. Chem. Abstracts Volume 103, No. 71086p concerns the synthesis of (Z)-8-dodecen-1-ol and its acetate as pheromone components of the Oriental Fruit Moth (*Grapholita molesta*). This is an abstract of the article in Acta Chem. Scan Ser. B., 1985, B39(4), pages 267–72. U.S. Pat. No. 4,364,931 issued on Dec. 21, 1982 discloses the use of 9(Z)-tetradecen-1-ol acetate in attracting male white-line dart moths.

Chem. Abstracts Volume 80, 1974, at No. 117098f discloses the use of trans-6-nonen-1-ol acetate as an ovipositional attractant and stimulant of the melon fly. U.S. Pat. No. 2,254,665 issued on Sept. 2, 1941, on the other hand, discloses the use of aliphatic alcohols in general in repelling insects which aliphatic alcohols have from 10 to 14 carbon atoms. Examples of the aliphatic alcohols of U.S. Pat. No. 2,254,665 are all saturated, to wit:
dodecyl alcohol;
octol alcohol;
hexadecyl alcohol;
tetradecyl alcohol; and
undecyl alcohol.

U.S. Pat. No. 2,254,665 fails to disclose the use of unsaturated alcohols in insect repellent compositions.

Chem. Abstracts Volume 74, 1971 at No. 99419f discloses various nonenyl acetates as attractants for female melon flies (abstract of *J. Med. Chem.*, 1971, 14(3), pages 236–9 including trans-2-nonen-1-yl acetate.

Formulations exist in commerce which are said to provide candle body materials that are both perfuming and insect repellent but such formulations have yielded a candle body that is either insufficiently insect repellent or aesthetically displeasing from an organoleptic standpoint.

When a candle burns, the heat of its flame melts a small pool of the candle body material around the base of the exposed portion of the wick, and this molten material is drawn up through the wick by capillary attraction to fuel the flame. Thus, the process that takes place in the burning of a candle imposes rather stringent functional requirements upon the candle body material.

The material of a candle body must be rigid enough to support itself and a relatively long wick filament, but it should not be excessively brittle at low temperatures. Its melting point is critical in that it should liquify temperatures, to which, it can be raised by radiant heat from the candle flame. If its melting temperature is too low, the candle will drip or, in an extreme case, the entire candle body will melt, dropping the wick into a pool of molten material with the hazardous possibility that the surface of the pool will ignite when this happens. If too high a temperature is required to melt the body material, the flame will be starved because insufficient fuel will be drawn up through the wick, with the result that the flame will be too small to maintain itself. When molten, moreover, the candle body material must have a relatively low viscosity in order to insure that it will be capable of being drawn up through the wick by capillary action.

In addition to meeting these requirements the candle body material must burn with a flame that is both luminous and smokeless and such odors as are produced by its combustion should not be unpleasant and should preferably be faint.

The functional requirements outlined above have, of course, been met by various candle body materials that are well known in the art, but heretofore no known materials that meet these requirements has been both:

(a) Perfuming to the environment surrounding the burning candle; and (b) Adequately insect repellent to the environment surrounding the material at various enviromental temperatures at atmospheric pressure, from a temperature of about 0° C. up to a temperature of about 50° C. However, the desire for such a candle body material which is either transparent, opaque or translucent has long persisted where the candle composition is both insect repellent and perfuming on use.

An article by Burton, "Intrinsic mosquito repellency values of some chemical compounds" appearing in Volume 84, *American Perfumer and Cosmetics*, April 1969 at page 41, indicates that coumarin has a value of from 0.001 up to 0.003 micromoles per liter of air for 90% insect repulsion. It further states that indole has a property such that 0.004 up to 0.01 micromoles per liter of air of Indole are needed for 90% insect repulsion. On the other hand, the article by Burton indicates that a compound such as linalool requires 0.1 micromoles per liter of linalool per liter of air for 90% insect repulsion.

Nothing is stated in the Burton article which causes one to be taught that coumarin and indole taken in combination can be added to citronella oil or one or more methyl heptenones whereby the efficacy of the overall composition is maintained or increased and the overall concentration of insect repelling mixture is substantially diminished while at the same time causing an aesthetically pleasing aroma to be emanated from the burning candle on use.

Currently on the market are "citronella oil candles" containing approximately 1.5–3% citronella oil. On use these candles give off an essentially aesthetically displeasing aroma and are not quite effective in repelling insects as desired by the user.

U.S. Pat. No. 3,615,289 issued on Oct. 26, 1971 discloses candle compositions which may be transparent or pastel shaded which are adapted to incorporate perfumes without flashing during burning, and such compositions comprise as the basic components the mixture of (i) a thermoplastic polyamide resin formed from linoleic acid polymerized with a polyamine compound; (ii) an alkanol amide or alkanol amine; and (iii) a stearic acid compound. More specifically, U.S. Pat. No. 3,615,289 specifically discloses and claims a candle composition comprising about 15 to 35% by weight of a solid gel thermoplastic polymer which is a solid polyamide resin which is the soluble condensation product of an aliphatic dicarboxylic acid and an amine, the carboxyl and amino groups of adjacent mono units being condensed to an amide linkage in the polymer (and the resin may also be based on carboxylic and amine compounds having more than two carboxyl and amino groups respectively). At column 3, line 10 of U.S. Pat. No. 3,615,289 it is indicated that the candle contain about 0.4% by weight of a perfume material. Claim 3 at column 4 of U.S. Pat. No. 3,615,289 discloses a composition wherein 5 to 7% of the composition is replaced by a coumarin-indene copolymer resin. The insect repellency of compositions usable in U.S. Pat. No. 3,615,289 is not disclosed however.

U.S. Pat. No. 3,645,705 discloses a transparent candle body composition of matter which can contain:

(a) From about 35% up to about 85% by weight of an oil which is normally liquid at room temperature which may be light mineral oil and a natural oil;

(b) From about 7% up to 40% by weight of a long chain polyamide having a molecular weight between 6,000 and 9,000 and a softening point within the range of 185° C.–48° C. from about 7% up to about 30% by weight of an alcohol which may be a $C_8$ up to a $C_{12}$ primary alcohol.

At column 3, line 56 of U.S. Pat. No. 3,645,705 it is disclosed that an odor masking agent may be incorporated into the candle composition. Generally this disclosure is set forth at lines 30–44 of U.S. Pat. No. 3,645,705 thusly:

"The inclusion in the composition of certain alcohols that produce otherwise desirable properties may result in a material that burns with an acrid or pungent odor. In such cases a small amount of an odor masking agent can be incorporated in the composition. The material sold by Fritzche, Dodge and Olcott as its No. 41984 has been found satisfactory when incorporated in the compositon in amounts up to about 0.2 percent by weight. The odor-masking agent is desirable when less expensive alcohols are used and may be unnecessary if the alcohols are highly refined, but from the standpoint of cost, the use of the cheaper alcohols and an odor-masking agent is indicated and produced satisfactory results. If desired, a small amount of perfume can be added to the composition to complete the odor-masking effect."

Nothing in U.S. Pat. No. 3,645,705, however, discloses the applicability to the composition disclosed therein of insect repellent materials. Nothing discloses the use of a composition of matter in U.S. Pat. No. 3,645,705 which will be both a perfumant and an insect repellent.

U.S. Pat. No. 4,051,159 issued on Sept. 27, 1977 discloses a "shaped, self-supporting transparent fragrance emitting article comprising a high percentage of a thermoplastic polyamide resin having substantially uniformly dispersed therein a $C_{14}$–$C_{22}$ alkyl alcohol and a fragrance emitting material". U.S. Pat. No. 4,051,159 however, does not indicate that the compositions of matter disclosed therein are useful for the purposes of candles and particularly are useful for fragrant candles or insect repellent candles or candles which are both fragrance emitting and insect repellent.

Published Japanese patent application No. J57088-101 assigned to the Agency of Industrial Sci. Tech. of Japan discloses the use of benzal acetone, laevo-cavone and thymol as insect repelling materials contained in conjunction with an aromatic substance, silica gel, talc or a binder such as polyvinyl alcohol or carboxymethyl cellulose.

Published Japanese patent application No. J 57088-101 however, does not indicate that compositions of matter are useful for the purposes of candles and particularly, are useful for fragrant candles or insect repellent candles which are both fragrancy emitting and insect repellent in an efficacious manner. The abstract of published Japanese patent application No. J 57088-101 is as follows:

Insect repellent contains benzalacetone (I) as active component. (I) has an immediate effect used in combination with sublimating substance such as naphthalene and camphor. The ratio of blend of benzalacetone to the sublimating substance is 90:1–5:95. Optionally, an excipient such as silica gel, talc and binder such as PVA or CMC and aromatic substance can be added (I) can be put in a suitable vessel, can be prepared as as tablet, or can be supported on cloth or paper.

Benzalacetone has the melting point of 41°–42° C. and the boiling point of 260°–262° C. The saturated gas concentration of benzalacetone is 0.045 mg/l by gas chromatography and is one tenth that of laevo-carvone and one third that of thymol, and therefore it has long-lasting effect.

(I) is nontoxic to warm-blooded animals, and shows repelling effect for a long period of time. It is prepared in low cost, and can be stored in a plastic vessel, since it does not etch plastics. It is particularly effective in the repelling of insects for clothes, e.g., *Tinea pellionella*.

Furthermore, both humans and animals are annoyed by insects and this problem is so acute as to render certain regions essentially uninhabitable by man. Disregarding the annoyance, insect bites are often accompanied by profound and in some cases serious physiological effects. Many diseases, particularly those of tropical origin, are transmitted by means of insect bites. In spite of man's constant warfare against insects they still occur in large numbers and they continue to plague both man and animals. Insecticide chemists have devoted considerable time and effort to this problem. Thousands of compounds have been tested for their toxic effect upon insects. These compounds either act as stomach poisons or respiratory paralyzers and are effective in a number of instances.

Another approach to the problem, which has also been given considerable thought, is the development of substances which have a repellent effect upon the insects. These substances can be applied upon the host in a variety of manners and serve to prevent attacks by insects which under normal conditions are attracted to these individuals.

Toxicity and repellency are not usually correlated, and it does not follow that a substance toxic to the insect is in any way repellent to it. On the other hand materials that are repellent to insects are not generally toxic and in a number of cases effective repellents are actually harmless to insects.

In order to be effective for this purpose the substance must of course, possess a high degree of repellency. In addition they must not be toxic or harmful to the individual treated. In general, it is believed that repellents are irritating to the sensory mechanism of the insect. It does not follow that a substance possessing this sensory irritating effect upon insects has a similar effect upon humans or animals. In a number of instances substances which definitely repel insects are pleasing to man and substances repugnant to man are attractive to insects.

Nothing in the prior art, however, discloses the use of 1-nonen-3-ol having the structure:

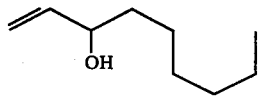

in repelling house flies (*Musca domestica*) or even infers that 1-nonen-3-ol has the highly efficacious ability to repel house flies (*Musca domestica*).

Indeed, the literature teaches away from our invention as exemplified in "Materials Tested as Insect Attractants" compiled by M. Berazo and N. Green in Agriculture Handbook No. 239 in Table 2 wherein it is stated that 3-methyl-1-nonen-3-ol (a homologue of 1-nonen-3-ol) has on a scale of 1 to 3 an attractancy of "1" for the Oriental Fruit Fly and an attractancy of "1" for the Mediterrean Fruit Fly and 4,8-dimethyl-7-nonen-4-ol has on a scale of 1 to 3 an attractancy of "2" for the Oriental Fruit Fly and an attractancy of "3" for the Mediterrean Fruit Fly and an attractancy of "1" for the Mexican Fruit Fly and an attractancy of "1" for Drosophila. With respect to any of the nonenol derivatives set forth therein the USDA Agriculture Handbook 239 indicates that the nonenol derivatives are neither attractants nor repellents for house flies (that is *Musca domestica*).

BRIEF DESCRIPTION OF THE DRAWINGS

FIG. 1 is a schematic diagram (blown up for illustration purposes) of the olfactometer apparatus useful in ascertaining the efficacy of the 1-nonen-3-ol as a repellent for house flies (*Musca domestica*) indicating in schematic block flow diagram form the utilization of computer assisted efficacy measuring apparatus.

FIG. 1A is a representation of one of the landing pad sections on plate 117 of the apparatus of FIG. 1 where the house flies (*Musca domestica*) land if and when they are attracted by the substance being tested, in this case 1-nonen-3-ol.

FIG. 2 is a cut-away side elevation schematic diagram of a screw extruder during the compounding of a polymer (e.g., polyethylene) with the 1-nonen-3-ol repellent while simultaneously adding foaming agent into the hollow portion of the barrel of the extruder and incorporates the pelletizing apparatus used in pelletizing the extruded foamed tow produced as a result of the extrusion operation.

SUMMARY OF THE INVENTION

Our invention is directed to the utilization of 1-nonen-3-ol per se and incorporated into a polymer body or candle body as a house fly (*Musca domestica*) repellent.

One aspect of our invention relates to the formation of 1-nonen-3-ol repelling articles, that is, articles useful for the repellent of house flies (*Musca domestica*) in combination with compatible polymers, e.g., high density polyethylene or low density polyethylene. Thus, one aspect of the invention provides a process for forming 1-nonen-3-ol-containing polymeric particles such as foamed polymeric pellets which include a relatively high concentration of 1-nonen-3-ol.

Thus, one aspect of our invention relates to the formation of 1-nonen-3-ol polymeric pellets by means of introduction into a single screw or twin screw extruder of, in series, thermoplastic polymer followed by 1-nonen-3-ol which is compatible with the thermoplastic polymer, in turn, (optionally) followed by introduction of a gaseous blowing agent or blowing agent which will produce a gas which is inert to the polymer and to the 1-nonen-3-ol previously introduced into the extruder.

The advantageous of using a foamed polymeric particle are multiple, to wit: improved handling, greater retention of 1-nonen-3-ol when not in use; greater length of time during which release of 1-nonen-3-ol from the polymer is at "steady state" or "zero order".

The nature of the extruder utilized in the process of our invention to form the polymeric 1-nonen-3-ol-containing polymer particles of our invention may be either single screw or double screw. Thus, the types of extruder that can be used are disclosed at pages 246–267 and 332–349 of the Modern Plastic Encyclopedia, 1982–1983, published by the McGraw-Hill Publishing Company, the disclosure of which is incorporated by reference herein. More specifically, examples of extruders which are usable in carrying out one of the processes of our invention (with modification for introduction of the 1-nonen-3-ol) downstream from introduction of the polymer and with further modification that the gaseous blowing agent is introduced still further downstream from the point of introduction of the 1-nonen-3-ol are as follows:

1. The Welex "Super Twinch" 3.5" extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kans. 67277;
3. Modified Sterling model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;

6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff single screw, twin screw, or foam extrusion equipment manufactured by Berstorff Corporation, P.O. Box 240357, 8200-A Arrowridge Blvd., Charlotte, N.C. 28224.

In producing the 1-nonen-3-ol polymer particles of our invention various polymers may be utilized, for example, low density polyethylene high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are ethylene vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E. I. duPont de Nemours Company under the tradename "ELVAX®" and by the Arco Polymer Division under the trademark "DYLAND" and by the Exxon Corporation of Linden, N.J. under the trademark "DEXXON". Ethylene/ethyl acrylate co-polymers are marketed by Union Carbide Corporation under the tradename "EEA RESINS".

The polymer is added to the single screw or twin screw extruder at a feed rate in the range of from about 80 up to about 300 pounds per hour while maintaining the temperature of the screw extruder between about 160° and about 240° C. If the polymer or co-polymer powder is added to the extruder at a reference "barrel segment", then the 1-nonen-3-ol is added to the extruder under pressure downstream from the addition point of the polymer at 1 or more of "barrel segments" S-2, S-3, S-4, S-5, S-6, S-7, S-8 or S-9.

The proportion of 1-nonen-3-ol to resin can vary from small but effective amounts on the order of about 1% of the weight of resin body up to about 45% by weight of the resin body. In general it is preferred to use between about 5% up to about 30% based on the weight of the resin body of 1-nonen-3-ol. This is an optimum amount balancing the proportion of 1-nonen-1-3-ol against the time period over which the article emits the 1-nonen-3-ol and against the tendency of the 1-nonen-3-ol to "oil out". This "oiling out" is specifically avoided as a result of use of the foaming agent discussed, infra.

Various polymers are useful in the practice of our invention. Specific examples of polymers useful in the practice of our invention are as follows:

(a) DYLAN® brand of low density polyethylene DYLAN® is a trademark owned by the Atlantic Richfield Company of Los Angeles, Calif.;

(b) DYLITE® of expandable polystyrene compositions. DYLITE® is a trademark of the Atlantic Richfield Company of Los Angeles, Calif.;

(c) SUPER DYLAN® a high density polyethylene. SUPER DYLAN® is a trademark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated by reference herein;

(f) Polyene/alpha-olefin as exemplified and disclosed in U.S. Pat. No. 4,369,291, the specification for which is incorporated by reference herein;

(g) Poly-alpha-olefins as exemplified in Canadian Letters Patent No. 1,137,069 issued on Dec. 7, 1982, the specification for which is incorporated by reference herein;

(h) Polymeric compositions as disclosed in Canadian Letters Patent No. 1,137,068 issued on Dec. 7, 1982, the specification for which is incorporated by reference herein;

(i) Poly-alpha-olefins disclosed in Canadian Letters Patent No. 1,137,067, the specification for which is incorporated by reference herein;

(j) Polyolefins described in Canadian Letters Patent No. 1,137,066, the specification for which is incorporated by reference herein;

(k) Polyethylene oxides as disclosed in Canadian Letters Patent No. 1,137,065 issued on Dec. 7, 1982, the specification for which is incorporated by reference herein;

(l) Olefin polymers and co-polymers as disclosed in Canadian Letters Patent No. 1,139,737, the disclosure of which is incorporated by reference herein. Canadian Pat. No. 1,139,737 was issued on Jan. 18, 1983;

(m) Polyolefins disclosed in Canadian Letters Patent No. 1,139,738, the disclosure of which is incorporated by reference herein. Canadian Pat. No. 1,139,738 was issued on Jan. 18, 1983;

(n) Chlorinated PVC as disclosed in *Polymer* 1982, 23 (7, Suppl.), 1051-6 abstracted at Chem. Abstracts 97: 145570y, 1982;

(o) Polyepsilon caprolactone co-polymers made by means of alcohol initiated polymerization as disclosed in *J. Polym. Sci. Polym. Chem. Ed.* 1982, 20(2), pages 319-26, abstracted at Chem. Abstracts, Volume 96: 123625x, 1982;

(p) Styrene acrylonitrile co-polymers as disclosed in Diss. Abstracts, Int. B, 1982, 42(8), 3346 and abstracted at Chem. Abstracts 96: 143750n (1982);

(q) Co-polymers of epsilon caprolactone with 1,4-butane diol as disclosed at Kauch. Rezine, 1982, (2), 8-9, abstracted at Chem. Abstracts, Volume 96: 182506g (1982);

(r) Polyesters as disclosed in U.S. Pat. No. 4,326,010, the specification for which is incorporated by reference herein;

(s) Chlorinated polyethylene as disclosed by Belorgey, et al., *J. Polym. Sci.* Polym. Phys. Ed. 1982, 20(2), 191–203; (t) Plasticized polyepsilon caprolactone co-polymers containing dimethyl phthalate plasticizers as set forth in Japanese Pat. No. J81/147844, abstracted at Chem. Abstracts, Volume 96: 69984y (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Downstream from the addition point of the 1-nonen-3-ol, optionally, the gaseous or liquid containing blowing agent may be added (e.g., at barrel segments S-5, S-6, S-7, S-8, S-9 or S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed 1-nonen-3-ol-containing particle.

The feed rate range of 1-nonen-3-ol may be between about 0.5% to about 45% by weight of the polymer.

The die of the extruder may create rod, sheet, film or ribbon. The resulting product may then, if desired, be pelletized to form 1-nonen-3-ol-containing polymer particles or the ribbon may be used "as-is" as an 1-nonen-3-ol-containing polymeric article of manufacture itself.

In addition to the optional gaseous blowing agents (which are necessarily "inert" gases), blowing agents may be added at the same point on the extruder which will create gaseous voids in the 1-nonen-3-ol-containing polymer articles of our invention and these "blowing agents" are well known to one having ordinary skill in the art. Examples of such non-gaseous containing materials which yield gases on admixture with the polymer in the extruder but which are still inert to the insect attractant are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFCl_3$, $CF_2Cl_2$, $CH_3Cl$, $CH_2$, $Cl_2$ separately or in admixture with one another as set forth in U.S. Pat. No. 3,758,425, column 4, lines 1-5, the specification for which is incorporated by reference herein;

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which are incorporated herein by reference; and (iv) Azo bis(formamide); diazoaminobenzene; N,N'-dinitrosopentamethylene tetramine; N,N'-dimethyl-N,N'-dinitrosoterephthalamide; p,p'-oxy-bis(benzene sulfonyl semicarbazide); azo bis(isobutyronitrile); p,p'-oxy-bis(benzene sulfonyl hydrazide); p,p'-diphenyl-bis(-sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be for example injection molded to form a useful article. Such injection molding can be carried out in accordance with the procedure as set forth in U.S. Pat. No. 3,268,636 issued on Aug. 23, 1966, the specification for which is incorporated by reference herein.

In addition, our invention relates to candle body materials which on use are both insect repellent and perfuming in which contain 1-nonen-3-ol in order to repel house flies (*Musca domestica*).

The house fly repellent-perfuming compositions which form part of the candle body materials are within the following specifications:

(I) from 5 up to 100% by weight of an efficacious perfuming/insect repellent composition consisting essentially of 1-nonen-3-ol; and (II) from 0 up to 95% by weight of a standard perfuming substance (non-insect repellent) which may be one or a combination of the following materials:

the methyl ester of 2,5-dihydroxy-4,6-dimethyl benzoic acid;
dihydro myrcenol;
oakmoss absolute;
benzyl acetate;
geraniol;
isobornyl acetate;
citronellyl acetate;
para-t-butyl phenyl isovaleraldehyde;
benzyl salicylate;
hexyl cinnamic aldehyde;
geranotrile;
patchouli oil;
alpha-terpineol'
tetrahydromuguol;
phenyl ethyl alcohol;
cedrenal;
methyl ionone;
cinnamyl acetate;
benzyl benzoate;
L-Citronellal;
Nerol;
Geranyl formate;
Geranyl acetate;
Eugenol;
Alpha Farnesene;
Beta Farnesene;
Citral;
n-Nonanal;
n-Octanal;
Trans, trans delta-damascone;

The foregoing formula may require a solubilizing agent, e.g., the methyl ester of dihydroabietic acid (commercial name: HERCOLYN D ®, benzyl benzoate, isopropyl myristate and/or $C_{12}-C_{14}$ isoparaffin hydrocarbons.

The candle base composition can be standard paraffin wax, or it can be transparent or pastel shaded as more particularly described in U.S. Pat. No. 3,615,289 issued on Oct. 26, 1971 (the disclosure of which is incorporated by reference herein) and wherein the candle body comprises as the basic components a mixture of:

(i) a thermoplastic polyamide resin formed from linoleic acid polymerized with a polyamine compound;

(ii) an alkanol amide or alkanol amine; and (iii) a stearic acid compound.

The weight of ratio of candle body: 1-nonen-3-ol/perfumant substance of our invention may vary from about 0.8% up to about 10% with a range of from about 0.8% up to about 2.0% being preferred when no non-insect repelling perfume oil is used in conjunction with the 1-nonen-3-ol; and with a range of from about 1.5% up to about 10% by weight of the overall composition being preferred when a non-insect repelling perfume oil is used in conjunction with the 1-nonen-3-ol.

Specifically, the polyamide may be a "Versamid" resin which is a thermoplastic condensation product of polymerized linoleic acid with various polyamine compounds such as ethylene diamine, ethylene triamine and the like. Specific "Versamid" compounds are "VERSAMID®900", "VERSAMID®930, "VERSAMID®940, "VERSAMID®948, "VERSAMID®950" and "VERSAMID®1635". These compounds are products of the Henkel Chemical Corporation of Minneapolis, Minn.

Another substance required in the clear candle composition consists of about 20-55% by weight of an alkanol amine or alkanol amide prepared by the reaction of a fatty acid ester and amine whereby the ester and the amine are in substantially equal proportions, for example, compounds such as Barlol 12C2 (manufactured by the Barrid Chemical Company) a monoalkyl diethanolamine have 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready incorporation of the insect repellent/perfumant compositions of our invention up to a level of approximately 5% (total proportion of perfume oil-insect repellent composition). They are carriers for the perfumant/insect repellent and may be used in a proportion of between 1 and 50% by weight of the composition although the preferable range is between 20 to 30%. In this connection it is possible to use up to about 10% by weight of perfumant/insect repellent if part of the formula is replaced by the material "Nevex 100", a product which is a coumarin-indene copolymer resin of very little unsaturation, manufactured by the Neville Chemical Company.

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperatures. Such a gel is disclosed in U.S. Pat. No. 3,645,705 issued on FEB. 29, 1972, the disclosure of which is incorporated by reference herein. Such compositions of matter include:

(a) from about 35% up to about 85% by weight of an oil which is normally liquid at room temperature chosen from the group consisting of light mineral oil and natural oils having iodine values substantially within the range of 40-135;

(b) from about 7% up to about 40% by weight of a long chain polyamide having a molecular weight substantially within the range of 6000-9000 and a softening point substantially within the range of 18° C.-48° C.; and (c) from about 7% to about 30% of an alcohol selected from the group consisting of 8 to 12 carbon primary alcohols.

Such composition may additionally include from about 1% up to about 15% of a methyl ester; up to about 5% by weight of stearic acid and up to about 5% by weight of an oxidation inhibiting agent and up to about 5% by weight of an acid selected from the group consisting of dimer and trimer acids.

Table I, set forth below, sets forth the results of the utilization of the olfactometer apparatus of FIG. 1 described in detail in the "Detailed Description of the Drawings" section, infra.

In this table the following abbreviated terms are used:
ACT.: Strikes at landing pad (Reference Numeral 110a in FIG. 1 and FIG. 1A).
TOT (%): Percent of total strikes per run.
(%)ACT-BLK: Percent activity excluding blank.
(%)ACT-POS.C: Percent activity minus percent of positive control.
FACTOR (ACT/CON): Ratio of activity divided by activity of positive control.

TABLE I

| ACT | TOTAL (%) | (%) ACT. -BLK. | (%) ACT -POS.C | FACTOR (ACT/CONT) |
|---|---|---|---|---|
| 348.0 | 9.500000 | 10.500000 | −7.500000 | 0.600000 |
| 286.0 | 6.100000 | 6.700000 | −11.500000 | 0.400000 |
| 3.0 | 1.600000 | 1.900000 | −16.500000 | 0.100000 |
| 15.0 | 1.300000 | 1.500000 | −18.600000 | 0.100000 |
| 7.0 | 1.200000 | 1.500000 | −12.500000 | 0.100000 |
| 1.0 | 0.700000 | 0.700000 | −10.400000 | 0.100000 |
| 2.0 | 0.500000 | 0.600000 | −24.000000 | 0.000000 |
| 1.0 | 0.200000 | 0.200000 | −20.100000 | 0.000000 |
| 6.0 | 0.100000 | 0.300000 | −72.200000 | 0.000000 |
| 0.0 | 0.000000 | 0.000000 | −2.800000 | 0.000000 |
| 0.0 | 0.000000 | 0.000000 | −20.100000 | 0.000000 |
| 55.0 | 2.000000 | 2.300000 | −16.200000 | 0.100000 |
| 117.0 | 3.500000 | 4.200000 | −17.900000 | 0.200000 |
| 90.0 | 5.000000 | 5.900000 | −14.200000 | 0.300000 |
| 22.0 | 2.400000 | 2.900000 | −19.800000 | 0.100000 |
| 2.0 | 1.100000 | 1.400000 | −36.400000 | 0.000000 |
| 6.0 | 0.800000 | 1.000000 | −10.700000 | 0.100000 |
| 42.0 | 4.600000 | 4.900000 | −15.000000 | 0.200000 |
| 1.0 | 0.100000 | 0.200000 | −5.500000 | 0.000000 |
| 7.0 | 0.900000 | 1.000000 | −14.000000 | 0.100000 |
| 1.0 | 0.100000 | 0.100000 | −18.300000 | 0.000000 |
| 253.0 | 3.700000 | 4.000000 | −11.000000 | 0.300000 |
| 161.0 | 5.200000 | 5.400000 | −10.200000 | 0.300000 |
| 88.0 | 3.600000 | 4.000000 | −10.100000 | 0.300000 |
| 3.0 | 0.700000 | 0.800000 | −5.300000 | 0.100000 |
| 15.0 | 1.100000 | 1.400000 | −21.200000 | 0.100000 |
| 7.0 | 1.500000 | 1.700000 | −20.900000 | 0.100000 |
| 17.0 | 2.200000 | 2.300000 | −14.900000 | 0.100000 |
| 972.0 | 7.600000 | 8.300000 | −3.100000 | 0.700000 |
| 69.0 | 2.200000 | 2.700000 | −22.300000 | 0.100000 |
| 47.0 | 2.200000 | 2.500000 | −13.200000 | 0.200000 |
| 1.0 | 0.500000 | 0.500000 | −25.900000 | 0.000000 |
| 30.0 | 2.200000 | 2.500000 | −11.900000 | 0.200000 |
| 345.0 | 7.200000 | 7.800000 | −4.600000 | 0.600000 |
| 498.0 | 9.900000 | 10.700000 | 1.000000 | 1.100000 |
| 128.0 | 4.500000 | 5.200000 | −6.300000 | 0.500000 |
| 4.0 | 0.700000 | 0.900000 | −13.400000 | 0.100000 |
| 39.0 | 1.500000 | 1.800000 | −12.700000 | 0.100000 |
| 3.0 | 0.700000 | 0.800000 | −19.000000 | 0.000000 |

TABLE I-continued

| ACT | TOTAL (%) | (%) ACT. -BLK. | (%) ACT -POS.C | FACTOR (ACT/ CONT) |
|---|---|---|---|---|
| 18.0 | 2.500000 | 2.700000 | −18.700000 | 0.100000 |
| 14.0 | 1.500000 | 1.800000 | −15.500000 | 0.100000 |
| 2.0 | 0.400000 | 0.500000 | −14.900000 | 0.000000 |
| 4.0 | 0.100000 | 0.500000 | −12.100000 | 0.000000 |
| 2.0 | 0.100000 | 0.100000 | −11.600000 | 0.000000 |
| 0.0 | 0.000000 | 0.000000 | −18.400000 | 0.000000 |
| 2.0 | 0.300000 | 0.300000 | −7.700000 | 0.000000 |
| 0.0 | 0.000000 | 0.000000 | −9.800000 | 0.000000 |
| 165.0 | 4.300000 | 4.800000 | −7.400000 | 0.400000 |
| 90.0 | 4.958678 | 5.859375 | −14.192708 | 0.292208 |
| 117.0 | 3.506143 | 4.195052 | −17.891717 | 0.189935 |
| 22.0 | 2.404372 | 2.910053 | −19.841270 | 0.127907 |
| 2.0 | 1.149425 | 1.398601 | −36.363636 | 0.037037 |
| 42.0 | 4.590164 | 4.918033 | −14.988290 | 0.247059 |
| 55.0 | 2.027772 | 2.344416 | −16.197783 | 0.126437 |
| 6.0 | 0.757576 | 1.020408 | −10.714286 | 0.086957 |
| 7.0 | 0.909091 | 0.980392 | −14.005602 | 0.065421 |
| 1.0 | 0.147710 | 0.172117 | −5.507745 | 0.030303 |
| 161.0 | 5.193548 | 5.444707 | −10.246872 | 0.346983 |
| 88.0 | 3.594771 | 4.003640 | −10.054595 | 0.284790 |
| 253.0 | 3.675189 | 3.979865 | −10.964291 | 0.266316 |
| 3.0 | 0.721154 | 0.835655 | −5.292479 | 0.136364 |
| 1.0 | 0.108696 | 0.118624 | −18.268090 | 0.006452 |
| 30.0 | 2.186589 | 2.544529 | −11.874470 | 0.176471 |
| 47.0 | 2.231719 | 2.460733 | −13.193717 | 0.157191 |
| 17.0 | 2.245707 | 2.254642 | −14.854111 | 0.131783 |
| 69.0 | 2.238806 | 2.690058 | −22.261209 | 0.107813 |
| 7.0 | 1.461378 | 1.745636 | −20.947631 | 0.076923 |
| 15.0 | 1.110289 | 1.353791 | −21.209386 | 0.060000 |
| 498.0 | 9.910448 | 10.650128 | 1.005133 | 1.104213 |
| 972.0 | 7.565969 | 8.265306 | −3.129252 | 0.725373 |
| 345.0 | 7.205514 | 7.830232 | −4.630050 | 0.628415 |
| 128.0 | 4.537398 | 5.192698 | −6.328600 | 0.450704 |
| 1.0 | 0.469484 | 0.471698 | −25.943396 | 0.017857 |
| 18.0 | 2.486188 | 2.714932 | −18.702866 | 0.126761 |
| 39.0 | 1.542722 | 1.806392 | −12.737378 | 0.124204 |
| 14.0 | 1.545254 | 1.822917 | −15.494792 | 0.105263 |
| 4.0 | 0.744879 | 0.881057 | −13.436123 | 0.061538 |
| 3.0 | 0.650759 | 0.802139 | −18.983957 | 0.040541 |
| 2.0 | 0.267380 | 0.322061 | −7.729469 | 0.040000 |
| 2.0 | 0.415800 | 0.530504 | −14.854111 | 0.034483 |
| 4.0 | 0.143318 | 0.164813 | −12.072518 | 0.013468 |
| 2.0 | 0.086580 | 0.097561 | −11.560976 | 0.008368 |
| 0.0 | 0.000000 | 0.000000 | −9.796984 | 0.000000 |
| 1.0 | 0.735294 | 0.740741 | −10.370370 | 0.666667 |
| 15.0 | 1.270110 | 1.492537 | −18.606965 | 0.074257 |
| 348.0 | 9.451385 | 10.507246 | −7.487923 | 0.583893 |
| 3.0 | 1.612903 | 1.898734 | −16.455696 | 0.103448 |
| 0.0 | 0.000000 | 0.000000 | −20.149254 | 0.000000 |
| 7.0 | 1.151316 | 1.508621 | −12.500000 | 0.107692 |
| 2.0 | 0.478469 | 0.558659 | −24.022346 | 0.022727 |
| 1.0 | 0.199601 | 0.218341 | −20.087336 | 0.010753 |
| 0.0 | 0.000000 | 0.000000 | −2.800000 | 0.000000 |
| 286.0 | 6.143931 | 6.657356 | −11.499069 | 0.366667 |
| 6.0 | 0.148112 | 0.254022 | −72.226926 | 0.003505 |

DETAILED DESCRIPTION OF THE DRAWINGS

FIG. 1 is a blow up of the olfactometer apparatus used in testing the efficacy of 1-nonen-3-ol as a house fly (Musca domestica) attracting material. Air source 134 feeds air through line 135 through air distributor 136 onto base plate 117 containing insect landing sites 110. The base plate 117 is separated from the spacer 130 for the air lines 136 whereby the air lines 136 are held in place at positions 131 and 131a. Air exits through line 133a using exhaust fan 133. The olfactometer is assisted with computer apparatus shown in schematic form and block flow diagram form using reference numerals 120, 121, 123, 124 and 125. Dampers 111a and 111b hold base plate 117 in place horizontally when an insect lands on landing site 110, at surface 110a the landing is recorded electrically through a sensor shown in magnified form in FIG. 1A. The sensor 115 causes an electrical impulse to proceed through wire 118 and then through wire 119 to a multi-channel A-D converter 120 which is associated with analogue transducer 121 and digital computer 123 which is associalted with modem 124 and main frame 125 effecting a recording of the data which is set forth in Table I, supra.

FIG. 1A is a partial cross section taken along lines 1a—1a of FIG. 1 showing one specific landing site 110 having surface 110a on which the insect lands if attracted by the 1-nonen-3-ol or does not land if repelled by the 1-nonen-3-ol which is also located at specific landing sites. At other landing sites nothing is located (and these are the "control" landing sites). The olfactometer is mounted on a base on which the dampers 111a and 111b are located, namely base 112. Base plate 117 remains covered with aluminum foil 126 which has holes 127 and 127a corresponding to the landing sites 110 and 110a, respectively, so that any insects that are attracted to the landing sites are not distracted to any other areas on base plate 117.

FIG. 2 is a schematic cut-away elevation diagram of the extrusion and pelletizing apparatus useful in carrying out the process of our invention during the operation of said apparatus. Motor 15 drives the extruder screws located at 23A in barrel 16, the extruder being operated at temperatures in the range of about 150° up to about 250° C. At the beginning of the barrrel resin at source 12 together with processing aids at location 13 is added via addition funnel 14 into the extruder. Simultaneously (when the operation reaches "steady state"), 1-nonen-3-ol is added to the extruder at one two or more of barrel S-3, S-4, S-5, S-6, S-7 and S-8 of the extruder (which may be a twin screw or single screw extruder) at locations 18a, 18b, 18c and 18d, for example, by means of gear pump 23 from source 17. From source 19 into barrel segments S-5, S-6, S-7, S-8, S-9 and S-10, optionally, the gaseous or liquid blowing agents, e.g., nitrogen, carbon dioxide and the like as described, supra, are added simultaneously with the addition of the 1-nonen-3-ol. The feed rate range of resin is about 80–300 pounds per hour. The feed rate range of 1-nonen-3-ol is between 1 and 35% of the feed rate range of the resin. The blowing agent rate range (when the blowing agent is used) is such that the pressure of the gas or the pressure over the liquid being fed into the extruder is between about 50 and 200 psig. If desired, the extruded ribbon or cylinder may be passed through water bath 20 and pelletizer 21 into collection apparatus 21a.

EXAMPLE I

Paraffin Wax Candle Body

The following composition is prepared:

| INGREDIENT | PARTS BY WEIGHT |
|---|---|
| Paraffin wax | 95.0 |
| 1-Nonen-3-ol | 5.0 |

The paraffin wax is intimately admixed at 150° C. and 10 atmospheres pressure with the mixture of methyl heptenone coumarin and indole in an autoclave with intensive shaking. The autoclave pressure is maintained with a nitrogen atmosphere. At the end of the period of 1 hour the autoclave is depressurized, the autoclave is opened and the resulting mixture is poured into cylindrical candle molds containing wicks.

The resulting candles on use evolve an aesthetically pleasing aroma and, in addition, give rise to efficacious house fly repellency. The candles are effective in preventing house flies from entering a room in which one candle is burning for a period of 10 minutes, the said room having dimensions of 6'×15'×15' having a 3'×3' open portal adjacent to a house fly-infested region in the month of August in the temperate zone.

EXAMPLE II

A transparent candle base mixture is produced by intimately admixing the following ingredients:

| INGREDIENT | PARTS BY WEIGHT |
|---|---|
| VERSAMID ® 1635 | 34.0 |
| Barlol 12C2 | 51.0 |
| Butyl Stearate | 3.5 |
| NEVEX ® 100 | 5.0 |
| SPAN ® 60 | 1.5 |
| Isopropyl Isostearate | 4.0 |
| Isopropyl Myristate | 4.0 |

The foregoing mixture is placed in an autoclave and intimately admixed with a perfuming-insect repellent composition containing 1-nonen-3-ol at the rate of 8% by weight of the total candle base composition.

The autoclave is sealed and heated to 180° C. under 15 atmospheres pressure and maintained with vigorous shaking for a period of 5 hours. At the end of the 5 hour period the autoclave is depressurized (being under a nitrogen pressure atmosphere) and the autoclave is opened and the contents are then poured into cyclindrical candle molds four inches in height and two inches in diameter containing 0.125" wicks. The resulting candles have efficacious insect repellencies and have aesthetically pleasing aromas on use.

The candles are effective in preventing house flies from entering a room in which two candles have been burning for 15 minutes, the said room having dimensions of 6'×15'×15' and having a 3'×3' open portal adjacent a house fly-infested region in the month of August, in the temperate zone.

EXAMPLE III

The following candle base composition of matter is prepared:

| INGREDIENT | PARTS BY WEIGHT |
|---|---|
| Polyamide (VERSAMID ® 940 manufactured by the Henkel Chemical Corporation of Minneapolis, Minnesota) | 30.0 |
| Stearic acid | 5.0 |
| Methyl-12-hydroxy stearate | 5.0 |
| 10 Carbon primary alcohol (Continental Oil Company ALFOL ® 10) further (ALFOL ® is a trademark of Conoco Division of E.I. DuPont of Wilmington, Delaware) | 5.0 |
| Myristyl Myristate | 10.0 |
| Stearic hydrazide | 0.1 |
| 1-Nonen-3-ol | 4.0 |
| Light white mineral | q.s. to 100% |

All of the materials except the polyamide are mixed at room temperature. The mixture is then heated gradually with gradual addition of the polyamide and with agitation beginning with the commencement of addition of the polyamide. In the proportion required, the polyamide does not become fully soluble until the mixture reaches the temperature of about 220° F. The temperature on the order of 220° F. to 230° F. is maintained at atmospheric pressure with continued agitation until the polyamide is fully dissolved. Since higher temperatures promote solution of the polyamide this temperature range can be slightly exceeded with some advantage. As soon as the polyamide has dissolved completely, the mixture is poured into molds following the conventional practice in the manufacture of molded candles. As the candles cool they harden. The candles are then freed from the molds and tested for insect repellency.

The candles are effective in preventing house flies from entering a room in which two candles have been burning for 15 minutes, the said room having dimensions of 6'×15'×15' and having a 3'×3' open portal adjacent a house fly-infested region in the month of August in the temperate zone.

EXAMPLE IV

A study was conducted to evaluate the efficacy of candles which are designated as "A", "B", and "C" in repelling house flies (*Musca domestica*).

Candle "A" contained 95% Paraffin Wax and 5% of the following composition:
100 parts by weight of 1-nonen-3ol; and
700 parts by weight of a perfume composition containing the following ingredients:

| INGREDIENT | PARTS BY WEIGHT |
|---|---|
| (i) Perfume mixture of essential oils and chemicals, to wit: the methyl ester of 2,5-dihydroxy-4-6-dimethyl benzoic acid; dihydro myrcenol; oakmoss absolute; benzyl acetate; geraniol; isobornyl acetate; citronellyl acetate; para-t-butyl phenyl isovaleraldehyde; benzyl salicylate; hexyl cinnamic aldehyde; geranonitrile; patchouli oil; alpha-terpineol; tetrahydromuguol; phenyl ethyl alcohol; cedrenal; methyl; ionone; cinnamyl acetate; benzyl benzoate; | 83.8 grams |
| (ii) Solvent: the methyl ester of dihydroabietic acid | 4.0 grams |

Candle "B" contained 90% Paraffin Wax and 10% citronells oil.

Candle "C" contained only Paraffin Wax.

The candles are allowed to burn for 20 minutes and the number of house flies repelled is recorded for the next 60 minutes with the following equipment and procedure:

MATERIALS

Test Chamber

The evaluation was conducted in a 28.3 cubic meter chamber with airing ports. A screened cage measuring 15 cm×15 cm×47.5 cm was attached inside an upper airing port, and a screened repellency observation cage measuring 15 cm×15 cm×32.5 cm was attached outside the upper airing port. The two cages were held together by a Masonite plate which fit firmly in the airing port. A 4-cm hole located in the center of each Masonite plate provided an escape for the test insects. A barrier was used to close the hole.

Attractant

A caged mouse was used as an attractant and was placed inside the chamber in the larger section of the repellency cage.

and the two screened repellency cages were submerged in hot detergent water, rinsed and dried.

RESULTS

The average percent of house flies repelled for each 5-minute exposure period through 60 minutes is reported in Table II.

TABLE II

| | | | House Flies Repelled at Five-Minute Time Intervals (20 Minutes Post Exposure | | | | | | | | | | | |
|---|---|---|---|---|---|---|---|---|---|---|---|---|---|---|
| Sample | Replicate | Number of House Flies | Cummulative Number of House Flies Repelled at Indicated Minutes | | | | | | | | | | | Overall Percent |
| | | | 10 | 15 | 20 | 25 | 30 | 35 | 40 | 45 | 50 | 55 | 60 | |
| Untreated | 1 | 93 | 1 | 1 | 1 | 1 | 1 | 2 | 2 | 3 | 3 | 4 | 6 | 6.45 |
| (no candle | 2 | 67 | 0 | 1 | 2 | 3 | 5 | 6 | 6 | 6 | 6 | 7 | 7 | 10.45 |
| used) | 3 | 86 | 2 | 2 | 2 | 3 | 4 | 6 | 6 | 7 | 7 | 7 | 7 | 8.14 |
| | 4 | 90 | 2 | 3 | 3 | 3 | 3 | 4 | 5 | 5 | 5 | 5 | 5 | 5.56 |
| Total | | 336 | 5 | 7 | 8 | 10 | 13 | 17 | 19 | 21 | 21 | 23 | 25 | |
| Average Percent | | | 1 | 2 | 2 | 3 | 4 | 5 | 6 | 6 | 6 | 7 | 7 | 7.44 |
| A | 1 | 108 | 2 | 5 | 7 | 8 | 8 | 8 | 8 | 10 | 10 | 10 | 12 | 11.11 |
| | 2 | 95 | 0 | 5 | 5 | 6 | 7 | 7 | 9 | 11 | 12 | 12 | 16 | 16.84 |
| | 3 | 86 | 3 | 6 | 8 | 8 | 10 | 10 | 11 | 11 | 12 | 12 | 13 | 15.12 |
| | 4 | 96 | 2 | 3 | 5 | 6 | 9 | 11 | 11 | 14 | 16 | 17 | 17 | 17.71 |
| Total | | 385 | 7 | 19 | 25 | 28 | 34 | 36 | 39 | 46 | 50 | 51 | 58 | |
| Average Percent | | | 2 | 5 | 6 | 7 | 9 | 9 | 10 | 12 | 13 | 13 | 15 | 15.06 |
| B | 1 | 80 | 4 | 5 | 7 | 7 | 8 | 8 | 9 | 9 | 9 | 10 | 11 | 13.75 |
| | 2 | 100 | 2 | 4 | 5 | 6 | 7 | 10 | 11 | 11 | 11 | 12 | 12 | 12.00 |
| | 3 | 87 | 2 | 2 | 3 | 4 | 5 | 5 | 6 | 6 | 6 | 6 | 7 | 8.04 |
| | 4 | 91 | 2 | 4 | 5 | 6 | 6 | 6 | 7 | 7 | 7 | 9 | 10 | 10.99 |
| Total | | 358 | 10 | 15 | 20 | 23 | 26 | 29 | 33 | 33 | 33 | 37 | 41 | |
| Average Percent | | | 3 | 4 | 6 | 6 | 7 | 8 | 9 | 9 | 9 | 10 | 11 | 11.45 |
| C | 1 | 79 | 6 | 8 | 8 | 8 | 8 | 8 | 8 | 8 | 8 | 9 | 10 | 12.66 |
| | 2 | 86 | 3 | 5 | 5 | 6 | 6 | 6 | 6 | 6 | 7 | 7 | 8 | 9.30 |
| | 3 | 92 | 2 | 4 | 4 | 5 | 7 | 7 | 7 | 7 | 7 | 7 | 8 | 8.70 |
| | 4 | 91 | 0 | 1 | 1 | 2 | 2 | 2 | 4 | 6 | 7 | 7 | 9 | 9.89 |
| Total | | 348 | 11 | 18 | 18 | 11 | 23 | 23 | 25 | 27 | 29 | 30 | 35 | |
| Average Percent | | | 3 | 5 | 5 | 6 | 7 | 7 | 7 | 8 | 8 | 9 | 10 | 10.06 |

Test Insect

Adult house flies (*Musca domestica*) are test insects.

Procedure

For each replicate, 75 to 100 adult house flies were removed from the rearing cage by means of a vacuum aspirator, and transferred by carbon dioxide anesthesia to the inner cage containing the mouse. The assembled cage was placed in one of the upper ventilation ports of the chamber.

For each experimental situation the test insects were transferred to a clean cage containing the mouse. A house fly candle was placed centrally on the chamber floor and burned for 20 minutes before initiating the repellency counts. The maximum period for the repellency counts was 60 minutes. The first repellency count was made at 10 minutes after the burning ended, and subsequent counts were taken at 5-minute intervals thereafter. The number of house flies repelled were those escaping to the outside cage. For the control, counts were made in a similar manner, but no candle was burned.

The same three candles were used for all four replicates. Between replicates the chamber was exhaused, the Kraft paper flooring for the chamber was replaced, The results of this experiment show that the candle containing 1-nonen-3-ol composition (2.5% of the total weight) is about 40% more efficacious from an insect repellency standpoint than a candle containing 10% citronella oil . . . and in addition, such candles containing the 1-nonen-3-ol composition on burning yield an aesthetically pleasing scent which is totally unlike the 10% citronella oil containing candle which yields an aesthetically displeasing scent.

What is claimed is:

1. A candle comprising a molded hydrocarbon wax composition having a protruding wick embedded therein said molded hydrocarbon wax composition consisting essentially of:
    (a) crystalline paraffin wax; and
    (b) an insect repelling quantity of 1-nonen-3-ol.

2. The candle of claim 1 comprising in addition a non-insect repelling quantity of a non-insect repellent perfume.

3. A process of imparting perfuming and *Musca domestica* repelling properties to a candle comprising the steps of:
    (i) intimately admixing a crystalline paraffin wax with a composition of matter consisting essentially of:
        (a) from 1 up to 30 parts by weight of 1-nonen-3-ol; and
        (b) a non-insect repelling perfume composition; and
    (ii) fabricating the resulting mixture into a candle.

* * * * *